United States Patent [19]

Fischer et al.

[11] Patent Number: 4,788,055
[45] Date of Patent: Nov. 29, 1988

[54] RESINATE SUSTAINED RELEASE DEXTROMETHORPHAN COMPOSITION

[75] Inventors: Franz X. Fischer, Riehen; Satish C. Khanna, Bottmingen, both of Switzerland

[73] Assignee: Ciba-Geigy Corporation, Ardsley, N.Y.

[21] Appl. No.: 806,879

[22] Filed: Dec. 9, 1985

[51] Int. Cl.$^4$ ...................... A61K 31/74; A61K 31/44
[52] U.S. Cl. ...................................... 424/79; 514/289; 514/850
[58] Field of Search .................. 514/289, 850; 424/79

[56] References Cited

U.S. PATENT DOCUMENTS 2,990,332  6/1961  Keating .............................. 521/29 X
4,221,778  9/1980  Raghunathan ....................... 424/483
4,427,681  1/1984  Munshi ................................ 514/289

OTHER PUBLICATIONS

Remington's Pharmaceutical Sciences, 13th Edition, pp. 1625-1626.
Rohm and Haas Manufacture's Literature on Amberlite IRP69.
Amberlite Product Literature, Rohm & Haas (2/78).

Primary Examiner—Leonard Schenkman
Attorney, Agent, or Firm—Irving M. Fishman

[57] ABSTRACT

A pharmaceutical preparation for controlled, sustained release of dextromethorphan comprising a polystyrene sulfonate resin which has been cross-linked with about 3% to about 10% divinyl benzene, having an average particle size of at least 48 μm and less than 100 μm onto which dextromethorphan has been loaded in a ratio of dextromethorphan hydrobromid to resin of about 1:3 to about 1:10 and at least one pharmaceutically acceptable adjuvant.

20 Claims, No Drawings

RESINATE SUSTAINED RELEASE DEXTROMETHORPHAN COMPOSITION

The invention relates to the field of resinate sustained release compositions. A number of resinous materials have been known to form complexes with drug substances which are subsequently released in gastrointestinal media at a rate different from that demonstrated by conventional drug delivery systems. Such phenomena have been reported, particularly between weakly basic drugs and cationic sulfonic acid resins, in U.S. Pat. Nos. 2,990,332 and 4,221,778. While such systems have yielded reasonable results in some cases, other drug-resin complexes yield products having drug release rates which cannot be suitably controlled. As stated in U.S. Pat. No. 4,221,778, the uncoated complexes of U.S. Pat. No. 2,990,332 provide only a relatively short delay in drug release.

Therefore, it was generally believed that for drugs such as the narcotic analgesics and their related anti-tussives, uncoated resin complexes thereof were unsuitable as truly useful sustained release products. At the time the instant invention was made, it was believed that suitable resin-drug complexes for sustained release of dextromothorphan required a "different barrier coated" outer surface, e.g. according to U.S. Pat. No. 4,221,778, to retard the release of active agent.

Additionally, there are formulation and stability problems which are apparent in the art. While drug complexes according to U.S. Pat. No. 2,990,332 might give reasonably useful products in dry formulations, their utility in aqueous media is seriously curtailed. Since U.S. Pat. No. 2,990,332 indicates drug release in both gastric and intestinal fluids, it is apparent that drug release occurs over a very broad range of pH, and, given time, even at a pH close to neutral. Hence, products containing appreciable amounts of water with slightly basic or acidic compounds dissolved therein are viewed as unsuitable as vehicles for the drug-resin complex if a commercially reasonable shelf-life (more than 3 months, preferably greater than 6 months, more preferably more than 1 year) for a preformulated liquid medication is to be achieved. Upon storage in aqueous media, such as in an aqueous syrup or suspension, drug would be expected to readily dissociate itself from the resin resulting in a formulation containing free drug and free resin or resin having other formulation components bound thereto in place of some or all of the drug which should remain bound. Such a formulation obviously would not be expected to adequately perform the desired function of sustained release. Hence, it was even more strongly believed that the "diffusion barrier coatings" such as those disclosed in U.S. Pat. No. 4,221,778 were necessary.

It was an object of the instant invention to provide a dextromethorphan-resin drug complex suitable for incorporation into a liquid sustained release anti-tussive formulation.

A further object of the invention is to provide a dextromethorphan-resin complex which is stable against dissociation in aqueous media for a commercially reasonable shelf-life.

Another object of the invention is to provide a sustained release anti-tussive dextromethorphan liquid formulation.

DETAILED DESCRIPTION OF THE INVENTION

Surprisingly and unexpectedly, these and other objects, which are apparent from the following, have now been realized with a dextromethorphan formulation comprising a dextromethorphan complex of a resin comprising a polystyrene sulfonate resin which is cross-linked with about 3% to about 10% by weight of cross-linking agent, based on the total resin, which resin has an average particle size between 40 microns and 100 microns, the complex having a ratio of dextromethorphan hydrobromide to resin of from 1:3 to 1:10. This complex, remains stable to dissociation in typical aqueous formulations as set forth below and releases dextromethorphan in the gastro-intestinal tract in a controlled sustained release manner.

The resin is suitably a strong cationic exchanger having sulfonic acid groups on a polystyrene homo or co-polymer matrix. The polystyrene sulfonate copolymer is a copolymer of (1) a styrene, such as styrene or lower alkyl styrene, which has been sulfonated, and (2) at least one other vinyl monomer selected from the class of styrenes above, their unsulfonated analogs, the acrylic- and methacrylic esters and amides of monohydric linear or branched alcohols with from 1 to 20 carbon atoms, and which alcohols may be aliphatic, cycloaliphatic, or aromatic in nature, such as: methyl-, ethyl-, propyl-, iso-propyl-; n-, iso-, and tertiary butyl-; hexyl-, pentyl-, 2-ethylhexyl-, n-octyl-, 1,1,3,3-trimethylbutyl, decyl-, tridecyl-, hexadecyl-, stearyl-, cyclohexyl-, isobornyl-, dicyclopentadienyl-, menthyl-, dicyclopentadienylethyl-; phenyl-, benzyl-, methoxyethyl-, ethoxyethyl-, furfuryl-, glycidyl-, acrylate or methacrylate as well as the corresponding amides; and acrylonitrile;

vinyl esters, such as: vinyl acetate, vinyl propionate, and vinyl benzoate;

vinyl ethers such as: methyl-, propyl-, butyl-, and methoxyethyl-vinyl ether;

fumarate, maleate and itaconate diesters of the monohydric alcohol-residues mentioned above; or (3) another styrene copolymerizable monomer selected from acrylic and/or methacrylic acid or derivatives thereof, such as hydroxyalkyl esters where alkyl is 2 to 4 carbon atoms, e.g. 2-hydroxyethyl, 3-hydroxypropyl, 2-hydroxypropyl or 2,3-dihydroxypropyl esters; also ethoxylated and polyethoxylated hydroxyalkyl esters such as esters of alcohols of the formula

$$HO-C_mH_m-O-(CH_2CH_2-O)_n-H$$

where m represents 2 to 5 and n represents 1 to 20, or esters of analogous alcohols, wherein a part of the ethylene oxide units is replaced by propylene oxide units. Also suitable are 3-(dimethylamino)-2-hydroxypropyl esters and amides. Another class of suitable derivatives of such acids are their water-soluble amides, such as unsubstituted amides and amides substituted by lower hydroxyalkyl is 2 to 4 carbon atoms such as N-(hydropropyl-)acrylamide, N-(2-hydroxy-ethyl)methacrylamide and N-[1,1-dimethyl-2-(hydroxymethyl)-3-oxabutyl-]acrylamide; water soluble hydrazine derivatives, such as dimethyl-2-hydroxypropylamine methacrylimide and the corresponding derivatives of acrylic acid.

Also useful, in combination with comonomers, are the lower hydroxyalkyl maleic esters and vinyl ethers where alkyl is 2 to 4 carbon atoms, for instance, di-(hydroxyalkyl)maleates, such as di(2-hydroxytheyl)maleate, and ethoxylated hydroxyalkyl maleates, hydroxyalkyl monomaleates, such as 2-hydroxyethyl monomaleate and alkoxylated hydroxyalkyl monomaleate together with vinyl ethers, vinyl esters, styrene or generally any monomer which will easily copolymerize with maleates or fumarates; hydroxyalkyl vinyl ethers, such as 2-hydroxyethyl vinyl ether, 4-hydroxybutyl vinyl ether, together with maleates, fumarates, or generally all monomers which will easily copolymerize with vinyl ethers.

Other comonomers useful in this invention are: alkyl ethers of polyethoxylate hydroxyalkylesters of acrylic and methacrylic acid, such as esters of alcohols of the formula

wherein
m=2 to 5 and
n=4 to 20

Dialkylaminoalkyl esters and amides, such as 2-(dimethylamino)ethyl or 2-(diethylamino)ethyl acrylate and methacrylate, as well as the corresponding amides; amides substituted by lower oxa-alkyl or lower dialkylamino alkyl groups, such as N-(1,1-dimethyl-3-oxabutyl)acrylamide; hydrazine derivatives, such as trialkylamine methacrylimide, e.g., triethylamine-methacrylimide and the corresponding derivatives of acrylic acid. Monoolefinic sulfonic acids and their salts, such as sodium ethylene sulfonate, sodium styrene sulfonate and 2-acrylamido-2-methylpropanesulfonic acid; or monoolefinic derivatives of heterocyclic nitrogen-containing monomers, such as N-vinylpyrrole, N-vinylsuccinimide, 1-vinyl-2-pyrrolidone, 1-vinylimidazole, 1-vinylindole, 2-vinylimidazole 4(5)-vinylimidazole, 2-vinyl-1-methylimidazole, 5-vinylpyrazoline, 3-methyl-5-isopropenylpyrazole, 5-methylenehydantoin, 3-vinyl-2-oxazolidone, 3-methacrylyl-2-oxazolidone, 3-methacryl-yl-5-methyl-2-oxazolidone, 3-vinyl-5-methyl-2-oxazolidone, 2- and 4-vinylridine, 5-vinyl-2-methylpyridine, 2-vinylpyridine-1-oxide, 3-isopropenylpyridine, 2- and 4-vinylpiperidine, 2- and 4-vinylquinoline, 2,4-dimethyl-6-vinyl-a-triazine and 4-acrylylmorpholine.

However, the sulfonated styrenes comprise suitably at least 90%, preferably 90–97%, more preferably 92–94%, most preferably 92%, by weight of the resin. The resin is more preferably (other than the crosslinking agent) a homo polystyrene sulfonate, most preferably a homo poly(unsubstituted styrene)sulfonate. When a copolymer is employed, up to 5% of the primary monomer may be replaced with a non-sulfonated styrene or non-styrene monomer set forth above. Copolymers of two or more sulfonated styrenes may be used in any ratio as desired.

The resin is crosslinked with a crosslinking agent selected from difunctional compounds capable of crosslinking polystyrenes; these are commonly known in the art. Preferably, the crosslinking agent is a divinyl or polyvinyl compound.

These crosslinking compounds include di- or polyacrylates and methacrylates of diols and polyols, such as: linear or branched aliphatic diols such as ethylene glycol, 1,2-propylene glycol, 1,6-hexanediol, 1,4-butanediol, 1,4-butanediol, 1,4-butynediol; diethylene glycol; dipropylene glycol, di-pentylene glycol; polyethylene oxide glycol; polypropylene oxide-glycol, polytetramethylene-oxide glycol; poly-(ethylene oxide-copropylene-oxide)glycol; thiodiethylene glycol; the reaction-product of a diisocyanate (aliphatic, cycloaliphatic or aromatic) with twice the equivalent amount of hydroxyalkyl acrylates or methacrylates; the reaction products of isocyanate terminated prepolymers derived from poly-ester diols, poly-ether diols or polysiloxane diols as shown in the art of polyurethane technology, with from 500–10,000 MW, with twice the equivalent amount of hydroxyalkyl methacrylates. Other such di- and polysiloxane-di- and polyvinyl compounds are described in U.S. Pat. No. 4,136,250. The appropriate portions of said patents are incorporated herein by reference.

Examples of such crosslinking agents include: trimethylolpropane triacrylate, neopentylglycol diacrylate; pentaerythritol and dipentaerythritol di-, tri-, tetra-, penta-, hexa-acrylates; ethylene glycol and diethylene glycol acrylates; divinyl ether; divinylbenzene; allyl methacrylate; diallyl maleate; diallylamine; divinyl sulfone; triallyl cyanurate. Most preferably the cross-linking agent is divinylbenzene. The resin is cross-linked to an extent of about 3% to about 10%, preferably about 4% to about 8%, more preferably about 6% to about 8%, and most preferably about 8% by weight based on the total resin. The resin is made by means well known in the art.

The most preferably resin for complexing with dextromethorphan is commercially available under the trade name Amberlit IRP 69 (Rohm and Haas).

Average particle size of the resin is limited to between about 40 μm and 100 μm, preferably about 40 μm to about 80 μm, more preferably about 50 μm to about 70 μm. It is desirable that about 85%, preferably about 95%, and most preferably about 98% of the resin particles have sizes within the ranges set forth above. Adjustments within these ranges can be made to accomodate desired aesthetic qualities of the final formulation product. It is more preferable that the resin dextromethorphan complex have particle sizes within these ranges as well.

The dextromethorphan-resin complex has a ratio of dextromethorphan hydrobromide to resin of about 1:3 to about 1:10, preferably about 1:4 to about 1:8, most preferably about 1:6. The only limit to using ratios in excess of 1:10 is an economic and aesthetic one.

The dextromethorphan-resin complex is formulated into a suitable liquid vehicle containing water, and, as desired, additional solvent, thickeners, preservatives, coloring agents, flavoring agents, solubilizers, dispersants, and other typical adjuvants, all of which must be pharmaceutically acceptable.

A preferred formulation contains about 0.3 g to about 1.5 g, preferably about 1.0 g, of thickener; about 1 g to about 10 g, preferably about 2.5 g, of 1,2-propylene glycol as a dissolving agent; about 0.12 g to about 0.19 g, preferably 0.15 g, of at least one paraben preservative such as methyl paraben; about 0.05 g to about 0.2 g, preferably about 0.1 g, of sorbic acid; about 30 g to about 60 g, preferably 40 g, of a sugar alcohol solution; about 0.05 to about 0.2 g, preferably 0.1 g of an artificial sweetener; dextromethorphan-resin complex in an amount to yield a desired strength, preferably about 2.10 g (the amount of a 1:6 complex needed to deliver equivalent to 60 mg of dextromethorphan hydrobromide in a 20 ml adult 12 hour dose); and sufficient water to bring the volume up to 100 ml.

Suitable thickeners include: tragacanth; bentonite; acacia and lower alkyl ethers of cellulose (including the hydroxy and carboxy derivatives of the cellulose ethers); preferably tragacanth. Exemplaries of the paraben preservatives are $C_1$-$C_4$ alkyl paraben, preferably methyl, ethyl, propyl, and butyl paraben. Methyl and propyl paraben are most preferable. Preferably, both methyl and propyl paraben are present in the formulation in a ratio of methyl paraben to propyl paraben of from about 2.5:1 to about 7.5:1, preferably 4:1. The artificial sweetener is advantageously a form of saccharin or aspartame, preferably saccharin sodium; however, when desirable, equivalent sweetening amounts of other known sweetening agents may be substituted therefor. The sugar alcohol is preferably sorbitol.

The amount of the resinate in the formulation is sufficient to deliver, when administered at one dose every 12 hours, an antitussive effective amount of dextromethorphan over a period of approximately 12 hours to a patient in need of such administration. A typical adult dose of 20 ml will contain approx. 420 mg of resinate, to deliver equivalent to 60 mg of dextromethorphan hydrobromide when the drug:resin ratio is 1:6 and 2.10 g of resinate are present per 100 ml of formulation. The dosage can be altered analogously to that known for the administration of dextromethorphan which has not been complexed with resin, i.e. the typical 15 mg–30 mg/dose of dextromethorphan hydrobromide 1 to 4 times daily, becomes 5–20 ml once to twice daily. Of course, alteration of these values will be necessary when different drug:resin ratio resinates are employed. Modification thereof will be apparent to those of ordinary skill.

In addition to the resinate, further active ingredients may be incorporated into the antitussive formulation as desired. These typically will include antihistamines, decongestants, demulcents and other antitussives. These may be utilized as they are or modified for sustained release as well.

The invention will be further understood by reference to the following examples, which illustrate but do not limit the invention.

EXAMPLE 1

Preparation of the dextromethorphan-resin complex

Sulfonated polystyrene having 8% by weight divinyl benzene cross-links (Amberlit IRP 69-Rohm & Haas) is treated with 2N NaOH for 4 Hours at 50° C. to convert the available sulfonic acid groups to their sodium forms. The supernatant is decanted and the resin is washed 3–4 times with deionized water. The washed resin is filtered and dried to constant weight at 50° C. under vacuum.

10 g dextromethorphan hydrobromide and 60 g of the dry resin (calculated on a moisture free basis) are dispersed in deionized water and stirred at 50° C. for about 24 hours to obtain essentially total binding of dextromethorphan to the resin. Residual free dextromethorphan is checked at intervals with a UV-spectrophotometer. At the end point, residual free drug was found to be negligible. The resinate is filtered and dried to constant weight at 50° C. under vacuum to yield resinate #1.

EXAMPLE 2

The process of Example 1 is followed except that the amount of dextromethorphan hydrobromide was altered so that resinates 2–4 (see below) were prepared.

| Resinate # | Drug/Resin |
|---|---|
| 2 | 1:5 |
| 3 | 1:4 |
| 4 | 1:3 |

EXAMPLE 3

Each of resinates 1–6 is screened and only the particles less than 100 microns in size are used. The release characteristics of resinates 1–4 are evaluated by the flow-cell method. An amount of each resinate containing the equivalent of 60 mg of active ingredient is placed in cells and an eluant is pumped therethrough at a constant rate of 16 ml/min. The free active ingredient in the eluent is then detected at various intervals. The eluent, for the first 60 minutes is artificial gastric fluid, (buffered at pH 1.2). Thereafter, the effluent is 0.9% saline solution.

The results are reported in Table I.

TABLE I

| Resinate | % release | | | | | |
|---|---|---|---|---|---|---|
|  | 1 hr. | 2 hr. | 3 hr. | 4 hr. | 5 hr. | 8 hr. |
| 1 | 13 | 38 |  | 65 | 74 | 88 |
| 2 | 16 | 44 |  | 71 | 78 | 91 |
| 3 | 24 | 48 |  | 74 | 81 | 93 |
| 4 | 30 | 60 |  | 81 | 90 | 97 |

Even after 5 hours, the resinates of the instant invention still have 10–26% of their original dose of active agent available for subsequent release. Still further, even after 8 hours, resinates 1 to 4 have 3–12% of the original dextromethorphan hydrobromide dose in reserve, making them quite suitable for once in 12 hour dosing.

EXAMPLE 4

Resinate is prepared in accordance with Example 1. The resinate is then screened into three particle size ranges: (1) less than (2) 40 μm, 40 μm, 40 μm–60 μm, and (3) 60 μm–100 μm. Each resinate size group is subjected to flow through cell testing under conditions (rate, eluent, time) analogous to those in Example 3; however, only resinate having a drug:resin ratio of 1:6 is utilized. The results demonstrate that as particle size decreases, a greater amount of drug is released initially per unit time. After 2 hours, 50% of the total drug reservoir is released from particles smaller than 40 μm, while particles between 40 and 60 μm release only 40%. After 8 hours, the smaller (less than 40 μm) particles release essentially 100% of their drug reservoirs, while the particles of 40 μm–60 μm still have a reservoir of nearly 15%.

EXAMPLE 5

Antitussive Preparation 2.10 g of the resinate of Example 1 is mixed with the following:

| Tragacanth | 1.00 g |
|---|---|
| Sorbitol | 40.00 g |

-continued

| | |
|---|---|
| Saccharin sodium | 0.10 g |
| 1,2-propylene glycol | 2.50 g |
| methylparben | 0.12 g |
| propylparben | 0.03 g |
| sorbic acid | 0.10 g |
| water sufficient to make 100 ml. (approx. 64 g) | | to arrive at an antitussive formulation having the equivalent of 60 mg of dextromethorphan hydrobromide per 20 ml.

What is claimed is:

1. An antitussive pharmaceutical composition suitable for controlled, sustained release of dextromethorphan comprising (a) a sulfonated polystyrene resin in salt-form crosslinked with about 3% to about 10% by weight (based on the total resin) of cross-linking agent, said resin having an average particle size of at least 40 $\mu$m and less than 100 $\mu$m, (b) an effective amount of a pharmaceutically acceptable acid addition salt of dextromethorphan, which has been loaded onto said resin in a weight ratio of dextromethorphan-acid addition salt:resin of about 1:5 to about 1:10, and (c) at least one pharmaceutically acceptable adjuvant.

2. The composition of claim 1 wherein said cross-linking agent is a di or poly acrylate or methacrylate of a diol, a divinyl compounds, or a diallyl compound.

3. The composition of claim 1 wherein said cross-linking agent is divinyl benzene.

4. The composition of claim 1 wherein said resin is crosslinked with about 4% to about 8% by weight, based on the total of preloaded resin, of crosslinking agent.

5. The composition of claim 1 wherein the salt form of said resin is the sodium salt form and said resin is crosslinked with about 8% by weight of divinyl benzene, based on the total preloaded weight of resin.

6. The composition of claim 5 wherein said average particle size is about 50 $\mu$m to about 70 $\mu$m.

7. The composition of claim 5 wherein at least 95% of said resin particles are of said average particle size.

8. The composition of claim 5 wherein said dextromethorphan-acid addition salt is detromethorphan hydrobromide.

9. The composition of claim 8 wherein said dextromethorphan hydrobromide:resin ratio is about 1:6.

10. The composition of claim 8 wherein said resin is a sulfonated polystyrene homopolymer which is crosslinked with about 8% of divinyl benzene, based on the preloaded weight of resin.

11. The composition of claim 1 wherein said average particle size of said resin in dry state is between about 40 $\mu$m and about 80 $\mu$m.

12. The composition of claim 1 wherein said ratio is 1:5–1:8.

13. The composition of claim 12 wherein said ratio is about 1:6.

14. The composition of claim 1 wherein said adjuvants are selected from pharmaceutically acceptable solvents, thickeners, sweeteners, flavorings, colorings, and preservatives.

15. The composition of claim 14 wherein
 (a) said solvent is water or a hydroalcoholic solution;
 (b) said thickener is selected from lower alkyl cellulose ethers, hydroxy and carboxy derivatives thereof; bentonite, tragacanth; and acacia;
 (c) said sweetener is selected from artificial sweeteners, mono and disaccharides, and sugar alcohols;
 (d) said preservative is selected from lower alkyl paraben, propylene glycol, and sorbic acid.

16. The antitussive composition of claim 14 comprising

| | |
|---|---|
| resinate | anti-tussive effective amount |
| tragacanth | 0.3 g–1.5 g |
| sorbitol | 30 g–60 g |
| artificial sweetener | 0.05 g–0.2 g |
| 1,2 propylene glycol | 1 g–10 g |
| paraben preservative | 0.12 g–0.19 g |
| sorbic acid | 0.05 g–0.2 g |
| solvent | sufficient to make 100 ml |

17. The anti-tussive composition of claim 16 comprising

| | |
|---|---|
| resinate (dextromethorphan hydrobromide:resin = 1:6) | 2.10 g |
| tragacanth | 1.00 g |
| sorbitol | 40.00 g |
| saccharin sodium | 0.1 g |
| 1,2 propylene glycol | 2.5 g |
| methyl paraben | 0.12 g |
| propyl paraben | 0.03 g |
| sorbic acid | 0.1 g |
| water | sufficient to make 100 ml |

18. The composition of claim 16 further comprising additional active ingredients.

19. The composition of claim 18 wherein said additional active ingredients are selected from antihistamines, decongestants, demulcents, analgesics, and further antitussives.

20. A pharmaceutical composition according to claim 1 wherein the pharmaceutically acceptable acid addition salt of dextromethorphan is the hydrobromide addition salt of dextromethorphan.

* * * * *